United States Patent
Hirono et al.

(10) Patent No.: US 9,683,947 B2
(45) Date of Patent: Jun. 20, 2017

(54) DEFECT INSPECTION DEVICE

(71) Applicant: NuFlare Technology, Inc., Yokohama (JP)

(72) Inventors: Masatoshi Hirono, Yokohama (JP); Riki Ogawa, Kawasaki (JP); Takeshi Fujiwara, Yokohama (JP)

(73) Assignee: NuFlare Technology, Inc., Yokohama-shi (JP)

( * ) Notice: Subject to any disclaimer, the term of this patent is extended or adjusted under 35 U.S.C. 154(b) by 0 days.

(21) Appl. No.: 15/000,715

(22) Filed: Jan. 19, 2016

(65) Prior Publication Data
US 2016/0209333 A1 Jul. 21, 2016

(30) Foreign Application Priority Data

Jan. 19, 2015 (JP) ................. 2015-008109

(51) Int. Cl.
*G01N 21/88* (2006.01)
*G01N 21/95* (2006.01)
*G03F 1/84* (2012.01)
*G01N 21/956* (2006.01)

(52) U.S. Cl.
CPC ....... *G01N 21/9501* (2013.01); *G01N 21/956* (2013.01); *G03F 1/84* (2013.01); *G01N 2021/95676* (2013.01); *G01N 2201/063* (2013.01)

(58) Field of Classification Search
CPC ........... G01N 21/8806; G01N 21/9501; G01N 2201/063; G01B 7/127; G01B 7/131
See application file for complete search history.

(56) References Cited

U.S. PATENT DOCUMENTS

| | | | | |
|---|---|---|---|---|
| 6,091,075 A * | 7/2000 | Shibata | ............ | G01N 21/9501 250/559.44 |
| 6,587,193 B1 * | 7/2003 | Reinhron | ........... | G01N 21/9501 356/237.5 |
| 6,762,831 B2 * | 7/2004 | Shibata | ............ | G01N 21/95607 250/559.42 |
| 6,806,971 B2 * | 10/2004 | Finarov | ............. | G01B 11/0616 250/339.08 |
| 2003/0227859 A1 * | 12/2003 | Hirai | ................ | G11B 7/127 369/112.12 |

(Continued)

FOREIGN PATENT DOCUMENTS

JP 2012-150036 8/2012

*Primary Examiner* — Sang Nguyen
(74) *Attorney, Agent, or Firm* — Oblon, McClelland, Maier & Neustadt, L.L.P.

(57) ABSTRACT

According to one embodiment, a defect inspection device includes a first beam splitter configured to branch light into a first optical path and a second optical path, a first optical system on the first optical path, a second optical system on the second optical path, a first aperture configured to form an illumination field of an inspection sample by light from the first optical system, a second aperture configured to form an illumination field of the inspection sample by light from the second optical system, and a third optical system configured to illuminate, with a first illumination, an image of the first aperture on a first area of the inspection sample, and to illuminate, with a second illumination, an image of the second aperture on a second area of the inspection sample.

16 Claims, 9 Drawing Sheets

First embodiment (56) References Cited

U.S. PATENT DOCUMENTS

| | | | |
|---|---|---|---|
| 2006/0012872 A1* | 1/2006 | Hayashi | G01N 21/21 359/386 |
| 2007/0070327 A1* | 3/2007 | Asundi | G01L 5/0047 356/32 |
| 2008/0186836 A1* | 8/2008 | Tanaka | G11B 7/126 369/112.24 |
| 2009/0129234 A1* | 5/2009 | Uno | G03H 1/26 369/103 |
| 2009/0316237 A1* | 12/2009 | Uno | G03H 1/02 359/1 |
| 2010/0271922 A1* | 10/2010 | Iwamura | G11B 7/1392 369/103 |
| 2012/0081685 A1 | 4/2012 | Kohl | |
| 2013/0342820 A1* | 12/2013 | Kajiyama | G03F 7/70358 355/67 |
| 2015/0001408 A1* | 1/2015 | Frank | G02B 26/0833 250/372 |

* cited by examiner

DEFECT INSPECTION DEVICE

CROSS-REFERENCE TO RELATED APPLICATIONS

This application is based upon and claims the benefit of priority from the prior Japanese Patent Application No. 2015-008109, filed Jan. 19, 2015, the entire contents of which are incorporated herein by reference.

FIELD

Embodiments described herein relate generally to a defect inspection device which optically inspects a defect in a plurality of kinds of patterns of an inspection sample.

BACKGROUND

A fine pattern of a semiconductor is formed by projecting, with reduction in size, a pattern etched on a photomask that serves like a negative of photography, or by using, like a stamp, a nano-imprint template on which a pattern of the same size is etched. In such a forming process, a defect inspection of a pattern, which serves as the original of the semiconductor, is very important.

In a general defect inspection device, telecentric optical systems and collimated optical systems are alternately arranged, and light is radiated on an inspection sample by an objective lens.

Here, if a maximum incidence angle of light rays to the inspection sample is expressed by θ and the refractive index of an image formation space is expressed by n, an NA of the optical system, that is, a numerical aperture, is defined as n sin θ. However, since the image formation space is usually in the air, n=1 and NA is expressed by sin θ. In addition, if the numerical aperture of illumination light is expressed by $NA_1$ and the numerical aperture of the objective lens is expressed by $NA_2$, the ratio $NA_1/NA_2$ thereof is called an illumination σ.

DETAILED DESCRIPTION

When the NA of an objective lens is maximum, the resolution limit performance of an optical system is theoretically highest in a case of σ=1. Actually, however, when a defect is to be detected, the optimal illumination σ depends on a pattern, and there is a case in which the capability of detection of a defect is higher when σ<1. Thus, in order to inspect under the condition that the capability of detection of a defect is maximum, an inspection sample in which patterns with different optimal illuminations σ are mixedly present, it is necessary to perform an inspection at least twice.

However, in an inspection device with high precision, such as a mask inspection device, if the illumination condition is varied, it is necessary to perform once again the adjustment of brightness of an inspection image, etc. In addition, a large ratio of inspection time is occupied by an acceleration/deceleration, a turn of a direction, etc. of a stage which moves the inspection sample. Thus, it is not desirable to perform an inspection a plurality of times.

Thus, the object of the invention is to provide a defect inspection device which can simultaneously inspect different areas with different illuminations σ with respect to an inspection sample on which a plurality of kinds of patterns are etched.

In general, according to one embodiment, a defect inspection device is configured to inspect a defect in a pattern of an inspection sample. The defect inspection device includes a light source, a first beam splitter configured to branch light from the light source into a first optical path and a second optical path, a first optical system disposed on the first optical path, a second optical system disposed on the second optical path, a first aperture configured to form an illumination field of the inspection sample by light which has passed through the first optical system, a second aperture configured to form an illumination field of the inspection sample by light which has passed through the second optical system, a third optical system configured to illuminate, with a first illumination, an image of the first aperture on a first area of the inspection sample, and to illuminate, with a second illumination that is different from the first illumination, an image of the second aperture on a second area different from the first area of the inspection sample, a first imaging element configured to acquire light of the first area, and a second imaging element configured to acquire light of the second area.

Various embodiments will be described hereinafter with reference to the accompanying drawings. In the description, common parts are denoted by like reference numerals throughout the drawings.

[1] First Embodiment

[1-1] Optical System 100 of Defect Inspection Device

Figure 1:
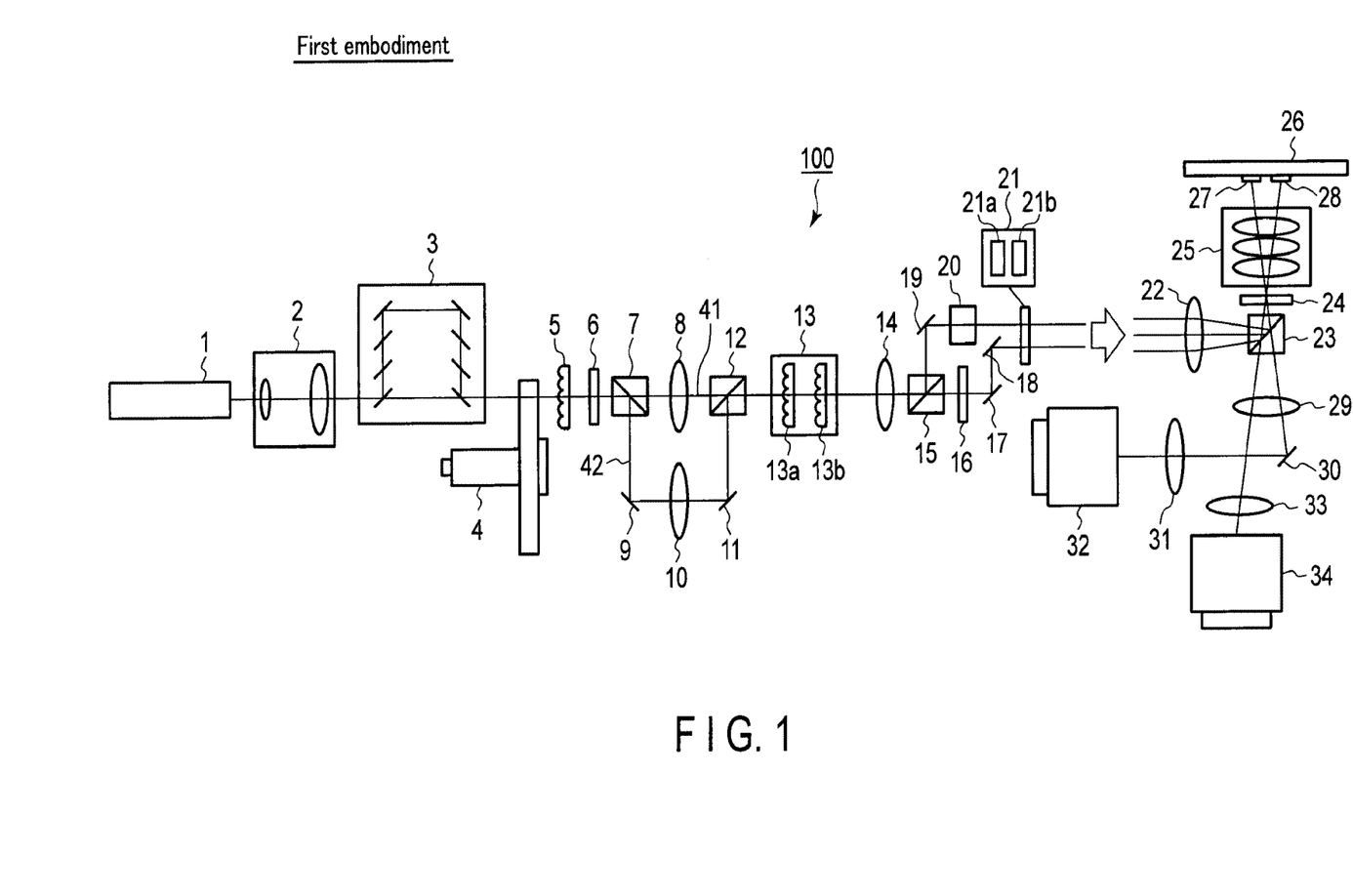
FIG. 1 is a view illustrating an optical system of a defect inspection device according to a first embodiment.

Referring to FIG. 1, an optical system 100 of a defect inspection device according to a first embodiment is described.

As a light source, a laser 1 is used. The beam diameter of a beam, which is emitted from the laser 1, is enlarged by an enlargement optical system 2, and speckle noise in an illumination field is reduced by a coherent reduction optical system 3 and a rotary phase plate 4. The light is divided by a microlens array 5 which forms a plurality of convergent points, and is converted to a plurality of divergent beams. It is now assumed that the polarization state of the beam is linear polarization, like a general laser.

The plural divergent beams are branched into an optical path 41 of P polarization light (transmissive light) and an optical path 42 of S polarization light (reflective light) by a polarizing beam splitter 7 disposed in front of a collective lens 8. The light amounts allocated to the respective optical paths 41 and 42 can arbitrarily selected by rotating a ½ wavelength plate 6 which is disposed in front of the polarizing beam splitter 7.

The transmissive light of the optical path 41 is collimated by the collective lens 8, and is made incident on a polarizing beam splitter 12. On the other hand, the reflective light of the optical path 42 is deflected by a miller 9, collimated by a collective lens 10, and further deflected by a miller 11. Then, the light of the optical path 41 and the light of the optical path 42 are made confluent by a polarizing beam splitter 12. In this manner, by the beam of the laser 1 being made to pass through the two optical paths 41 and 42, two different kinds of illuminations σ are generated.

The light, which has been made confluent by the polarizing beam splitter 12, illuminates a microlens array 13. The microlens array 13 is an image-side telecentric optical system. Specifically, for example, the microlens array 13 includes two microlens arrays 13a and 13b, and is configured such that a front-side focal point of the rear-side microlens array 13b coincides with the front-side microlens array 13a. In addition, the microlens array 13 is disposed at rear-side focal points of the collective lenses 8 and 10. By the optical system described thus far, the beam of the laser 1 is converted to divergent beams which are less coherent, uniform in intensity as a whole, and telecentric.

The respective divergent beams emanating from the focal point group of the microlens array 13 are collimated by a collective lens 14. Then, by a polarizing beam splitter 15, lights of two kinds of illuminations σ are branched once again.

P polarization light, which has passed through the polarizing beam splitter 15, is converted to S polarization light by a ½ wavelength plate 16 in order to uniformize the polarizations of the re-separated optical paths, is deflected by mirrors 17 and 18, and illuminates a rectangular diaphragm 21a of an aperture 21. On the other hand, S polarization light, which has been reflected by the polarizing beam splitter 15, is deflected by a mirror 19, and illuminates a rectangular diaphragm 21b of the aperture 21. At this time, the optical path lengths of the respective lights, which illuminate the two rectangular diaphragms 21a and 21b of the aperture 21, may be uniformized by using an optical path length correction element 20. Incidentally, the aperture 21 is disposed so as to coincide with a focal position of a collective lens 22, and forms illumination fields by the respective optical paths.

The light, which has passed through the two rectangular diaphragms 21a and 21b of the aperture 21, is Fourier-transformed by the collective lens 22, and is reflected by a polarizing beam splitter 23. Here, the polarizing beam splitter 23 reflects the light such that the light is incident on an inspection sample 26, with the optical axis of the light being perpendicular to the inspection sample 26.

The reflected light is converted to circularly polarized light by a ¼ wavelength plate 24, and images are formed by an objective lens 25 on different illumination fields 27 and 28 of the inspection sample 26. The objective lens 25 is disposed such that a rear-side focal point thereof coincides with the surface of the inspection sample. In this manner, the respective images of the aperture 21 are formed by illumination on the different illumination fields 27 and 28. Since the lights, which illuminate the two illumination fields 27 and 28, are the lights which have passed through the two different optical paths 41 and 42, the lights have different illuminations σ. Reflective lights from the illumination fields 27 and 28 are collected by the objective lens 25, are converted by the ¼ wavelength plate 24 into a polarization state that is orthogonal to the original state, and pass through the polarizing beam splitter 23, and images of the lights are formed by an image formation lens 29. In the meantime, unlike the case of using a non-polarizing beam splitter, the circular polarization illumination by the polarizing beam splitter 23 and ¼ wavelength plate 24 can separate illumination light and reflective light with a light use efficiency of about 100%.

The light, whose image was formed by the image formation lens 29, is separated by a mirror 30 which is disposed at a position conjugate to the inspection sample surface (the focal position of the image formation lens 29), and images are formed on cameras (imaging elements) 32 and 34 by collective lenses 31 and 33. The cameras 32 and 34 are disposed at positions of enlarged images of the inspection sample 26, which are formed by the collective lenses 31 and 33.

In the meantime, the front-stage microlens array 5 uniformizes the light intensity distribution of an incidence pupil surface of the objective lens 25, and the rear-stage microlens array 13 uniformizes the illuminance distribution of the inspection sample surface.

In the optical system 100 of the defect inspection device according to this first embodiment, the optical path 42, which is branched by the polarizing beam splitter 7, is longer than the original optical path 41. Thus, the focal distance of the collective lens 10 is made greater than the focal distance of the collective lens 8, in order to cause the collective lens 10 of the branch optical path 42, like the collective lens 8, to function as a collimator for the divergent beam formed by the microlens array 5, and in order to make the incidence surface of the microlens array 13 coincide with the rear-side focal point of the collective lens 10. Incidentally, the details of the collective lenses 8 and 10 will be described later.

In addition, in the present embodiment, the inspection sample 26 is illuminated such that the illumination fields 27 and 28 of the respective illumination lights, which have passed through the two optical paths 41 and 42, may not overlap. Thereby, inspection images, which are obtained by illuminating different positions of the inspection sample 26 with different illuminations σ, are independently detected by the different cameras 32 and 34.

[1-2] Collective Lenses 8 and 10

Figure 2:
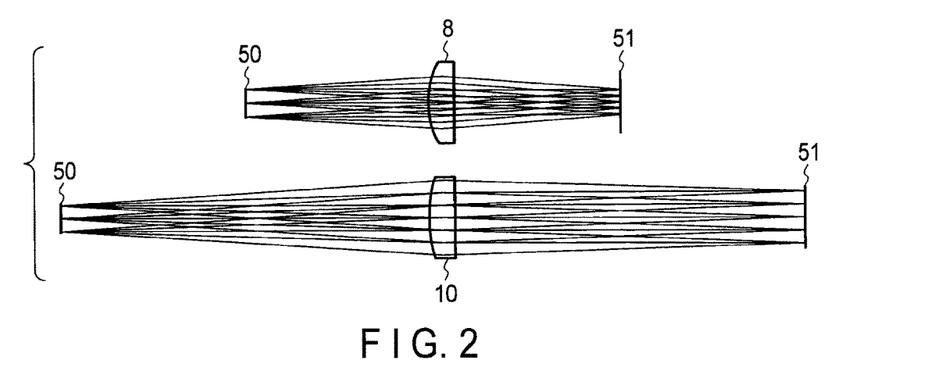
FIG. 2 is a view for explaining collective lenses with different focal distances according to the first embodiment.

Referring to FIG. 2, a description is given of the collective lenses 8 and 10 of the optical system 100 according to the first embodiment.

As illustrated in FIG. 2, as regards each of the collective lenses 8 and 10, the front-side focal point coincides with a focal point group 50 which is formed by the microlens array 5, and the rear-side focal point coincides with an incidence surface 51 of the microlens array 13. Here, since the branched optical path 42 is longer than the non-branched optical path 41, the focal distance of the collective lens 10 is greater than the focal distance of the collective lens 8.

In the collective lenses 8 and 10, the position and propagation direction of light rays at the front-side focal point are converted to the information pieces of the propagation direction and position of light rays at the rear-side focal point, respectively. Specifically, Fourier transform is executed by the collective lenses 8 and 10.

Here, the sizes of illumination fields at the incidence surface 51 are proportional to the focal distances of the collective lenses 8 and 10. Thus, the size of the illumination field at the incidence surface 51 of the collective lens 10 is greater than the size of the illumination field at the incidence surface 51 of the collective lens 8.

In addition, in the optical system of FIG. 1, since the focal point group of the microlens array 13 and the incidence pupil surface of the objective lens 25 are in the conjugate relationship, the illumination σ is proportional to the size of the illumination field of the incidence surface 51. Thus, the illumination σ of the optical system of the optical path 41 passing through the collective lens 8 becomes smaller, and the illumination σ of the optical system of the optical path 42 passing through the collective lens 10 becomes larger.

In this manner, in the first embodiment, by disposing the collective lenses 8 and 10 with different focal distances on the two optical paths 41 and 42, illuminations σ of two different conditions can be created on the inspection sample 26.

[1-3] Advantageous Effects

According to the above-described first embodiment, the collective lenses 8 and 10 with different focal distances are disposed on the two optical paths 41 and 42 which are branched by the polarizing beam splitter 7. Specifically, the focal distance of the collective lens 10 on the longer optical path 42 is made greater than the focal distance of the collective lens 8 on the shorter optical path 41. Thereby, on the incidence surface 51 of the microlens array 13, the size of the illumination field by the collective lens 10 can be made greater than the size of the illumination field by the collective lens 8. Here, since the focal point group of the microlens array 13 and the incidence pupil surface of the objective lens 25 are in the conjugate relationship, the illumination σ on the inspection sample 26 is proportional to the size of the illumination field of the incidence surface 51 of the microlens array 13. Thus, the illumination σ by the optical system of the optical path 41, on which the collective lens 8 is disposed, becomes smaller, and the illumination σ by the optical system of the optical path 42, on which the collective lens 10 is disposed, becomes larger.

In this manner, in the first embodiment, since the illuminations σ of two different conditions can be generated on the inspection sample 26, a defect inspection can be made at a time on patterns of two different areas with two different kinds of illuminations σ.

Moreover, when the two kinds of illuminations σ are generated, the optical system of FIG. 1 can be realized with a relatively minor alteration to the conventional optical systems. In particular, it is a great merit that the two kinds of illuminations σ can be realized without increasing microlens arrays 5 and 13 which are more expensive than other optical elements.

[2] Second Embodiment

In a second embodiment, a description is given of an optical system in which luminescent points on the incidence pupil surface of the objective lens 25 are arranged at more regular intervals than in the first embodiment.

[2-1] Manner of Arrangement of Luminescent Points on the Incidence Pupil Surface of Objective Lens 25

Figure 3:
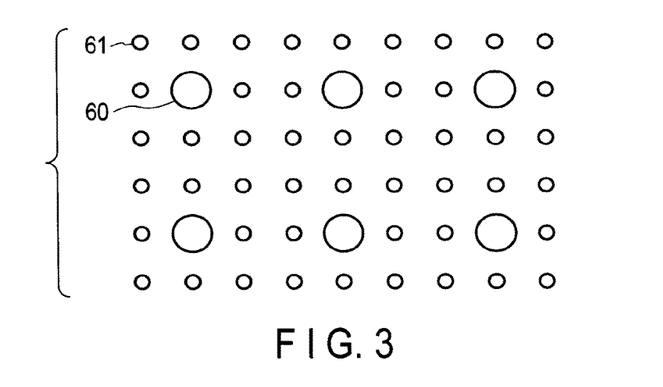
FIG. 3 is a view illustrating an arrangement of luminescent points which a non-branched optical system in FIG. 1 forms.
Figure 4:
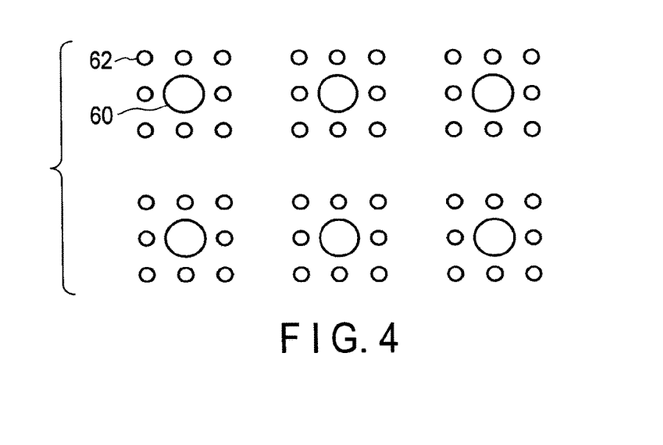
FIG. 4 is a view illustrating an arrangement of luminescent points which a branched optical system in FIG. 1 forms.

Referring to FIG. 3 and FIG. 4, a description is given of a manner of arrangement of luminescent points on the incidence pupil surface of the objective lens 25.

FIG. 3 illustrates an example of the manner of arrangement of luminescent points which a non-branched optical system forms, and FIG. 4 illustrates an example of the manner of arrangement of luminescent points which a branched optical system forms. Here, the non-branched optical system of FIG. 3 is the optical system 100 by the optical path 41 in FIG. 1. The branched optical system of FIG. 4 is the optical system 100 by the optical path 42 in FIG. 1.

In FIG. 3 and FIG. 4, a luminescent point (parent luminescent point) 60, which is expressed by a large circle, is created by a perpendicular incidence component of light that is incident on the rear-side microlens array 13. Luminescent points (child luminescent points) 61 and 62, which are expressed by small circles, are created by light that is obliquely incident on the rear-side microlens array 13. Here, it is assumed that the front-stage microlens array 5 is formed by 3×3 divisions.

It is desirable that the luminescent points 61 by the light that is obliquely incident on the microlens array 13 be designed to be arranged at regular intervals, as illustrated in FIG. 3.

However, as in the optical system of FIG. 1, if the luminescent points of one microlens array 5 are Fourier-transformed on the incidence surface of the microlens array 13 by the collective lenses 8 and 10 with different focal distances, the NA of illumination light, which passes through the collective lens 10 with the longer focal distance, is lower than the NA of illumination light, which passes through the collective lens 8 with the shorter focal distance, as is clear from FIG. 2. As a result, for example, if the arrangement of the luminescent points 60 and 61 by the collective lens 8 is designed to be at regular intervals, as illustrated in FIG. 3, there is a case in which the luminescent points 60 and 62 by the collective lens 10 are arranged such that the luminescent points 62 are arranged with higher density near each luminescent point 60. In the arrangement of luminescent points 60 and 62 as illustrated in FIG. 4, a frequency component of the microlens array 13 is conspicuous, and it is thus possible that an interference fringe occurs on the illumination field 27.

In this manner, in the case of the optical system 100 according to the first embodiment, such a case is thinkable that the luminescent points on the incidence pupil surface of the objective lens 25 are not arranged at regular intervals, leading to the occurrence of an interference fringe on the illumination field 27.

This being the case, in the second embodiment, there is proposed an optical system 100 of a defect instruction device, in which the luminescent points of both optical paths by the collective lenses 8 and 10 are arranged at regular intervals.

[2-2] Optical System 100 of Defect Inspection Device

Figure 5:
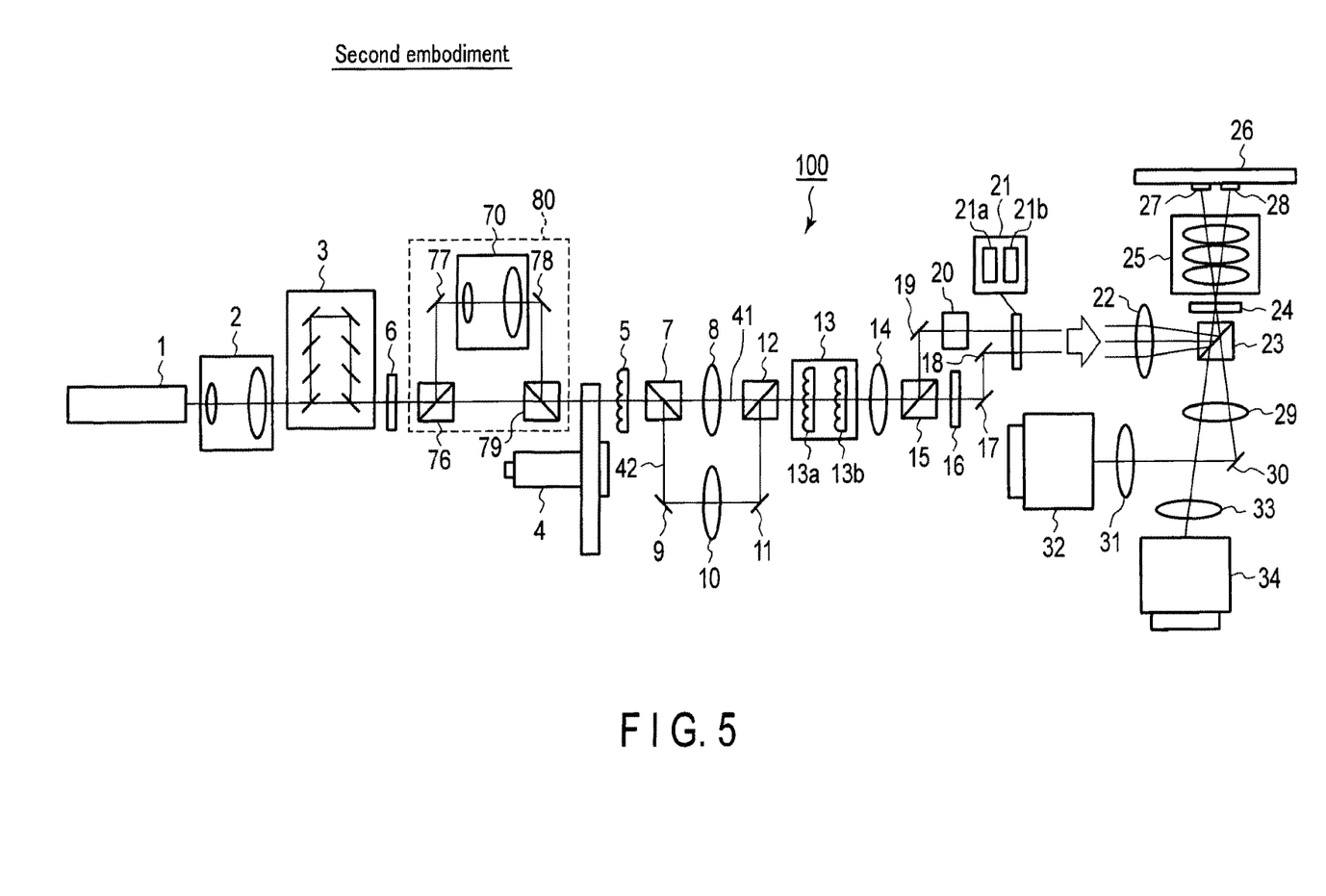
FIG. 5 is a view illustrating an optical system of a defect inspection device according to a second embodiment.

Referring to FIG. 5, an optical system 100 of a defect inspection device according to the second embodiment is described. Since the basic configuration of the optical system 100 of FIG. 5 is the same as in FIG. 1, different structural points will mainly be described below.

As illustrated in FIG. 5, in the second embodiment, an optical system 80 for increasing the beam diameter of light passing through the collective lens 10 is disposed in front of the front-side microlens array 5. This optical system 80 includes polarizing beam splitters 76 and 79, mirrors 77 and 78, and an enlargement optical system 70.

Specifically, the light from the light source 1 is branched by the polarizing beam splitter 76 into transmissive light (P polarization light) and reflective light (S polarization light). The reflective light is deflected by the mirror 77, the beam diameter of the reflective light is increased by the enlargement optical system 70, and the reflective light is further deflected by the mirror 78. Then, the transmissive light and reflective light are made confluent by the polarizing beam splitter 79, and the confluent light illuminates the microlens array 5.

Here, the NA of the light passing through the collective lens 10 is properly adjusted by the enlargement optical system 70 in accordance with the focal distance of the collective lens 10. In addition, it is desirable that the size of the microlens array 5 (the size of the effective area) be increased in accordance with the beam diameter that is increased by the enlargement optical system 70.

Incidentally, the light amounts, which are allocated to the transmissive light and reflective light (different illuminations σ) branched by the polarizing beam splitter 76, should better be adjusted by using the ½ wavelength plate 6. Thus, it is desirable that the ½ wavelength plate 6 be disposed in front of the polarizing beam splitter 76 which first executes polarization separation.

In addition, the large illumination σ passing through the collective lens 10 passes through a greater number of lens elements in the front-stage microlens array 5 than the small illumination σ passing through the collective lens 8. Thus, the number of child luminescent points of the large illumination σ becomes greater than the number of child luminescent points of the small illumination σ.

[2-3] Advantageous Effects

According to the above-described second embodiment, like the first embodiment, the collective lenses 8 and 10 with different focal distances are disposed on the two optical paths 41 and 42 which are branched by the polarizing beam splitter 7. Thereby, since the illuminations σ of different conditions can be generated on the inspection sample 26, a defect inspection can be made simultaneously on patterns of two different areas with two different kinds of illuminations σ.

In addition, in the second embodiment, the enlargement optical system 70 is disposed in front of the front-stage microlens array 5, and the beam diameter of the light passing through the collective lens 10 can be increased by this enlargement optical system 70. In this manner, by properly selecting the enlargement ratio of light passing through the collective lens 10 and the focal distance of the collective lens 10, the arrangement of luminescent points can be made equal between two kinds of illuminations σ. Thereby, the occurrence of an interference fringe on the illumination field 27 can be suppressed.

[3] Third Embodiment

In a third embodiment, the luminescent points on the incidence pupil surface of the objective lens 25 are arranged at regular intervals by an optical system 100 which is different from the optical system 100 of the second embodiment.

[3-1] Optical System 100 of Defect Inspection Device

Figure 6:
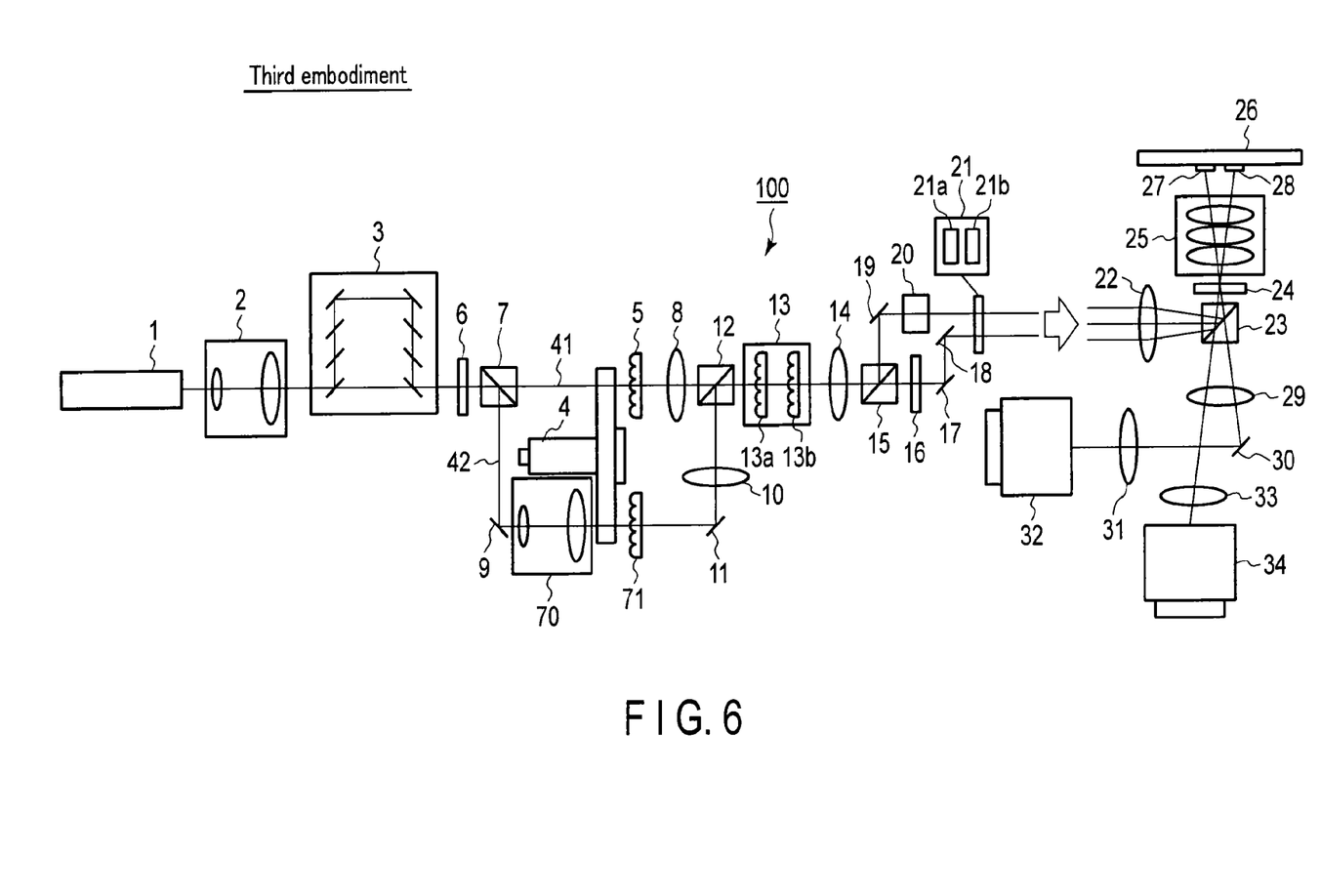
FIG. 6 is a view illustrating an optical system of a defect inspection device according to a third embodiment.

Referring to FIG. 6, an optical system 100 of a defect inspection device according to the third embodiment is described. Since the basic configuration of the optical system 100 of FIG. 6 is the same as in FIG. 1, different structural points will mainly be described below.

As illustrated in FIG. 6, in the third embodiment, polarization separation of light by the polarizing beam splitter 7 is executed in front of the rotary phase plate 4, and an enlargement optical system 70 for increasing the beam diameter of light passing through the collective lens 10 is disposed between the polarizing beam splitter 7 and the rotary phase plate 4.

Specifically, the light branched by the polarizing beam splitter 7 is deflected by the mirror 9, the beam diameter is increased by the enlargement optical system 70 in front of the rotary phase plate 4, and the light is made incident on a microlens array 71. This light is deflected by the mirror 11, passes through the collective lens 10, and is made incident on the polarizing beam splitter 12.

Here, by the enlargement optical system 70, the beam diameter of the light of the optical path 42 is made greater than the beam diameter of the light of the optical path 41. Thus, the size of the effective area of the microlens array 71 is larger than the size of the effective area of the microlens array 5. For example, the pitch of lenses may be made equal between the microlens array 71 and the microlens array 5, and the number of lenses of the microlens array 71 may be made greater than the number of lenses of the microlens array 5. In addition, although the microlens array 5 and microlens array 71 are composed of identical microlens arrays, only the inside area of the microlens array 5 may be utilized.

In the meantime, the front-side microlens arrays 5 and 71 are disposed near the rotary phase plate 4. Thereby, a greater amount of light, which is scattered by the rotary phase plate 4, can be taken into the front-side microlens arrays 5 and 71.

[3-2] Advantageous Effects

According to the above-described third embodiment, like the first embodiment, etc., the collective lenses 8 and 10 with different focal distances are disposed on the two optical paths 41 and 42. Thus, a defect inspection can be made simultaneously on patterns of two different areas with two different kinds of illuminations σ.

In addition, in the third embodiment, the enlargement optical system 70 is disposed in front of the collective lens 10 on the branch optical path 42. Thereby, the area of the focal point group 50 in FIG. 2 is enlarged, and the NA of illumination light on the incidence surface 51 of the rear-stage microlens array 13 can be increased. Thus, the arrangements of luminescent points of both the illumination optical system passing through the non-branched optical path 41 and the illumination optical system passing through the branched optical path 42 can be made equal, and the occurrence of an interference fringe on the illumination field 27 can be suppressed.

Furthermore, in the third embodiment, since the front-stage microlens array 71 is additionally provided, the price of the optical system 100 increases. However, an increase in price of the defect inspection device can be suppressed to a minimum, by suppressing the number of rotary phase plates 4 and the number of rear-stage microlens arrays 13, which are more expensive than other optical elements, to one, respectively.

[4] Fourth Embodiment

In a fourth embodiment, the luminescent points on the incidence pupil surface of the objective lens 25 are arranged at regular intervals by an optical system 100 which is different from the optical systems 100 of the second and third embodiment.

[4-1] Optical System 100 of Defect Inspection Device

Figure 7:
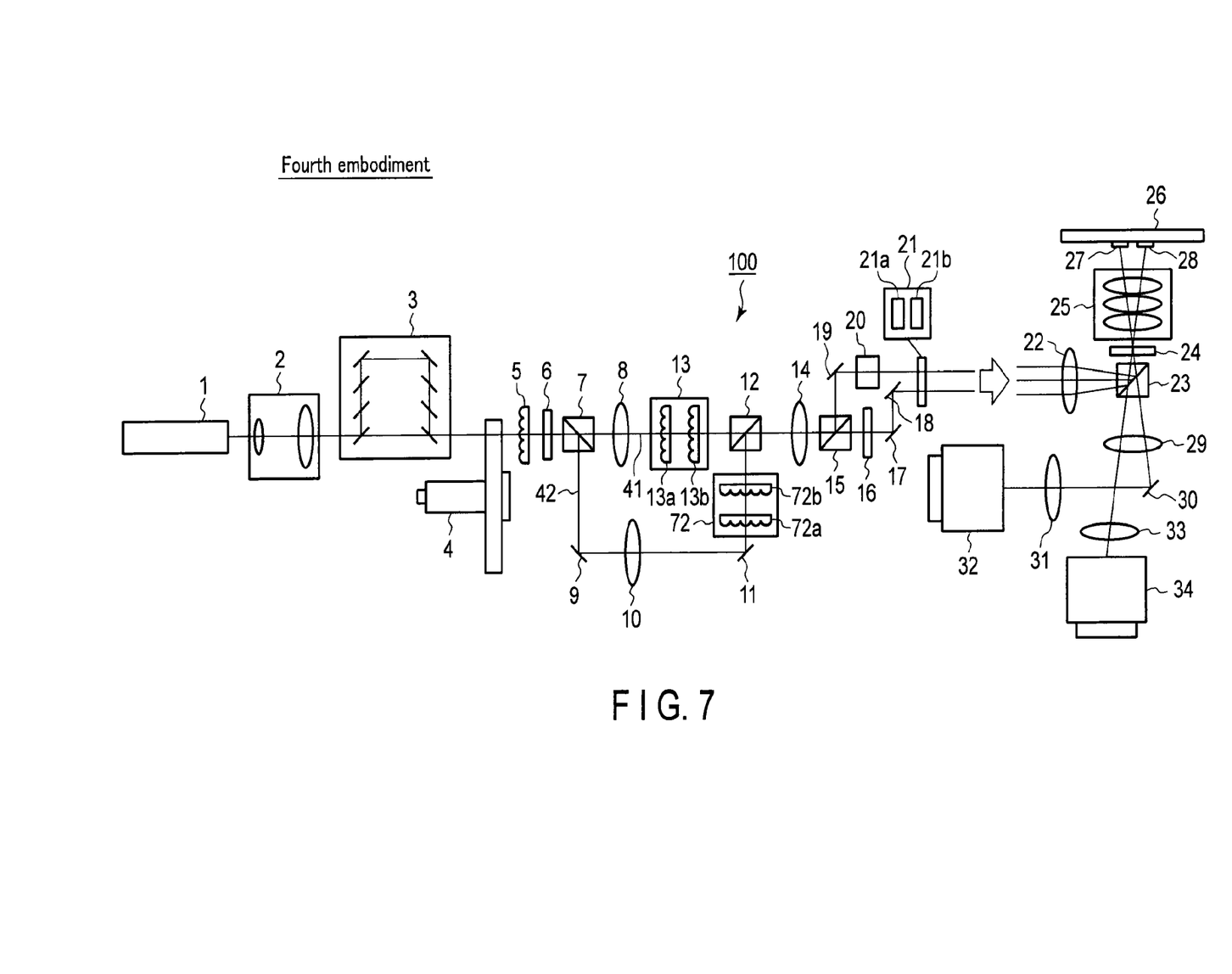
FIG. 7 is a view illustrating an optical system of a defect inspection device according to a fourth embodiment.

Referring to FIG. 7, an optical system 100 of a defect inspection device according to the fourth embodiment is described. Since the basic configuration of the optical system 100 of FIG. 7 is the same as in FIG. 1, different structural points will mainly be described below.

As illustrated in FIG. 7, in the fourth embodiment, rear-stage microlens arrays 13 and 72 are disposed between the collective lenses 8 and 10 and the polarizing beam splitter 12 on the respective optical paths 41 and 42.

The microlens array 72, like the microlens array 13, is an image-side telecentric optical system. Specifically, for example, the microlens array 72 includes two microlens arrays 72a and 72b, and is configured such that a front-side focal point of the rear-side microlens array 72b coincides with the front-side microlens array 72a. In addition, the microlens array 72 is disposed at a rear-side focal point of the collective lens 10. In addition, it is desirable that the pitch of elemental lenses of the microlens array 72 be narrower than the pitch of elemental lenses of the microlens array 13, and that the microlens array 72 have the same NA as the microlens array 13.

[4-2] Advantageous Effects

According to the above-described fourth embodiment, like the first embodiment, etc., the collective lenses 8 and 10 with different focal distances are disposed on the two optical paths 41 and 42. Thus, a defect inspection can be made simultaneously on patterns of two different areas with two different kinds of illuminations σ.

In addition, in the third embodiment, the intervals of luminescent points corresponding to the two illumination fields 27 and 28 are equal. By contrast, in the fourth embodiment, the rear-stage microlens arrays 13 and 72, which are set at predetermined NA's and lens pitches, are disposed between the polarizing beam splitter 12 and the collective lenses 8 and 10 on the optical paths 41 and 42. Thereby, the luminescent points of the high illumination σ, which are created via the optical path 42, can be uniformly arranged, although the pitch of the luminescent points of the high illumination σ becomes narrower than the pitch of the luminescent points of the low illumination σ, which are created via the optical path 41.

Furthermore, in the fourth embodiment, an increase in price of the defect inspection device can be suppressed to a minimum, by suppressing the number of front-stage microlens arrays 5 to one.

[5] Fifth Embodiment

In a fifth embodiment, the luminescent points on the incidence pupil surface of the objective lens 25 are arranged at regular intervals by an optical system 100 which is different from the optical systems 100 of the second to fourth embodiment.

[5-1] Optical System 100 of Defect Inspection Device

Figure 8:
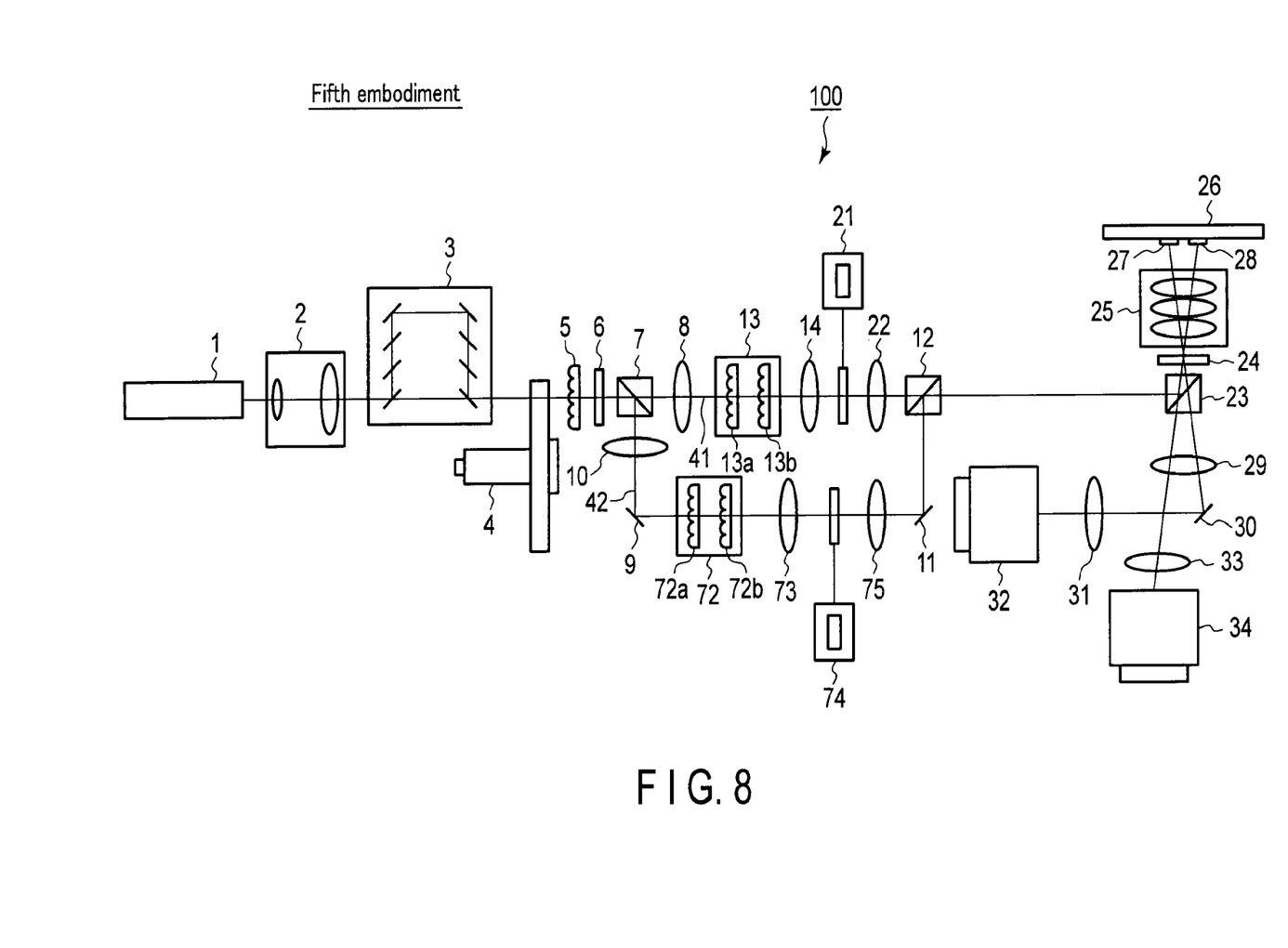
FIG. 8 is a view illustrating an optical system of a defect inspection device according to a fifth embodiment.
Figure 9:
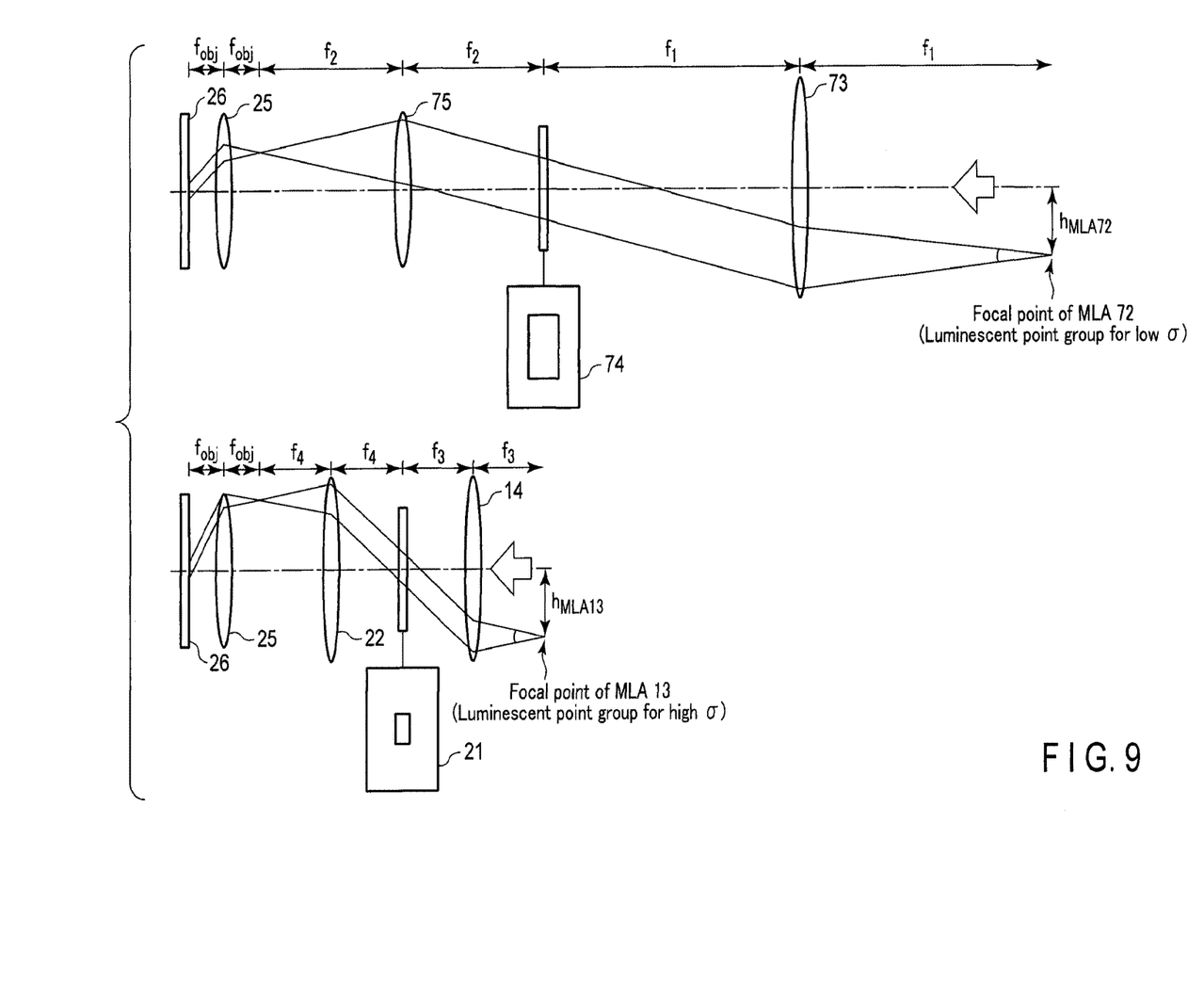
FIG. 9 is a schematic view illustrating a part of the optical system of FIG. 8.
Figure 10:
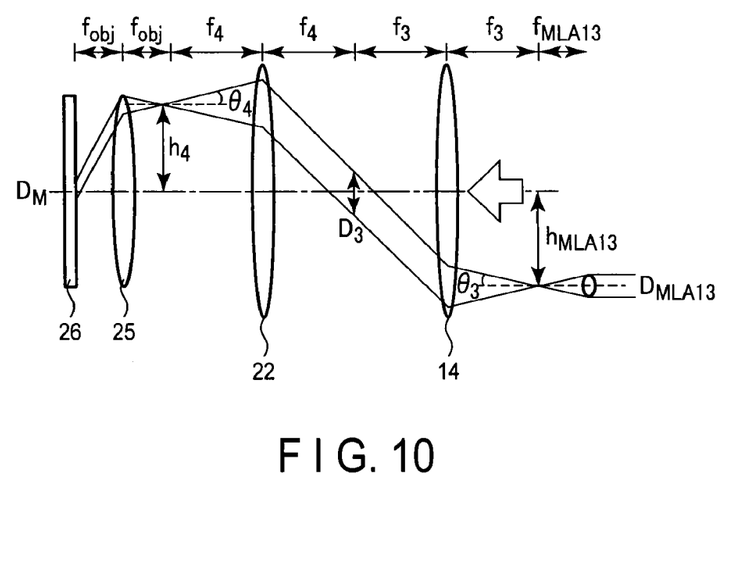
FIG. 10 is a view for explaining the relationship between a numerical aperture and an illumination in the optical system of FIG. 8.

Referring to FIG. 8 to FIG. 10, an optical system 100 of a defect inspection device according to the fifth embodiment is described. Since the basic configuration of the optical system 100 of FIG. 8 is the same as in FIG. 1, different structural points will mainly be described below.

As illustrated in FIG. 8, in the fifth embodiment, the optical paths 41 and 42, which are branched by the polarizing beam splitter 7, remain branched up to the polarizing beam splitter 12 in front of the object lens 25.

Specifically, on the optical path 41, the collective lens 8, microlens array 13, collective lens 14, aperture 21 and collective lens 22 are arranged in the named order. On the optical path 42, the collective lens 10, mirror 9, microlens array 72, collective lens 73, aperture 74, collective lens 75 and mirror 11 are arranged in the named order. In addition, the lights of the optical paths 41 and 42 are made confluent by the polarizing beam splitter 12.

Here, in the fifth embodiment, like the fourth embodiment, the focal distance of the collective lens 10 should better be made longer than the focal distance of the collective lens 8, and the pitch of elemental lenses of the microlens array 72 should better be narrower than the pitch of elemental lenses of the microlens array 13, so that the microlens array 72 may have the same NA as the microlens array 13.

However, in the fifth embodiment, two different kinds of illuminations σ may be created by using the collective lenses 8 and 10 of the same focal distance and properly setting the specifications of the optical system of the rear-stage microlens arrays 13 and 72 onwards.

Specifically, in this optical system 100, since the focal distances of the collective lenses 8 and 10 are equal, the incident beam sizes of the microlens arrays 13 and 72 become equal. In this case, the "pitch÷focal distance (=2NA)" should better be made different between the microlens arrays 13 and 72.

Specifically, as illustrated in FIG. 9, when the microlens array 13 generates a luminescent point group for high illumination σ and the microlens array 72 generates a luminescent point group for low illumination σ, it is desirable that the NA of the microlens array 13 be greater than the NA of the microlens array 72. The reason for this is as follows.

In an optical system with no substantial aberration as illustrated in FIG. 10, the relationship of the following equation (1) is established (Lagrange's invariant):

$$h_{MLA} \sin \theta_{MLA} = h_4 \sin \theta_4 = X \quad (1)$$

From FIG. 10, equation (1) can be rewritten to the following equation (2):

$$h_{MLA} D_{MLA}/2f_{MLA} = h_4 D_M/2f_{obj} = X \quad (2)$$

Taking this into account, if two optical systems of FIG. 9 are viewed, the value of X of the optical system is proportional to the illumination σ, and it is clear that the high illumination σ is greater.

Since $h_{MLA13}$ and $h_{MLA72}$ of the two optical systems of FIG. 9 are equal, these optical systems can be realized by setting NA=sin $\theta_{MLA}$ of the rear-stage microlens arrays 13 and 72 to be large for high illumination σ and to be small for low illumination σ.

In the meantime, when the collective lenses 8 and 10 of the same focal distance are used in the optical system of FIG. 8, it is desirable, as illustrated in FIG. 9, that a focal distance f3 of the collective lens 14 be shorter than a focal distance f1 of the collective lens 73, and that a focal distance f4 of the collective lens 22 be shorter than a focal distance f2 of the collective lens 75. Moreover, it is desirable that the size of the rectangular diaphragm of the aperture 21 be smaller than the size of the rectangular diaphragm of the aperture 74. In this case, however, since the child luminescent point becomes closer to the parent luminescent point in the case of the high illumination σ than in the case of the low illumination σ, it is difficult to equalize the intervals of luminescent points between both optical paths 41 and 42.

[5-2] Advantageous Effects

According to the above-described fifth embodiment, like the first embodiment, etc., the collective lenses 8 and 10 with different focal distances are disposed on the two optical paths 41 and 42. Thus, a defect inspection can be made simultaneously on patterns of two different areas with two different kinds of illuminations σ.

In addition, in the fifth embodiment, like the fourth embodiment, the rear-stage microlens arrays 13 and 72, which are set at predetermined NA's and lens pitches, are disposed behind the collective lenses 8 and 10 on the optical paths 41 and 42. Thereby, the luminescent points by the optical paths 41 and 42 can be arranged at regular intervals on the incidence pupil surface of the objective lens 25.

Furthermore, in the fifth embodiment, even if the optical systems up to the incident light of the rear-stage microlens arrays 13 and 72 are identical, the specifications of the optical systems of the rear-stage microlens arrays 13 and 72 onwards may properly be set, and thereby different luminances σ (the illumination size on the inspection sample 26 is identical) can be realized even with the same objective lens 25.

[6] Sixth Embodiment

In a sixth embodiment, a description is given of a defect inspection device using the optical system 100 of each of the above-described embodiments. This defect inspection device is a device which inspects a defect by using an image that is obtained by radiating light on an inspection sample, and, for example, a photomask, a master mask for NIL (Nano Imprint Lithography), etc. are used as inspection samples.

Figure 11:
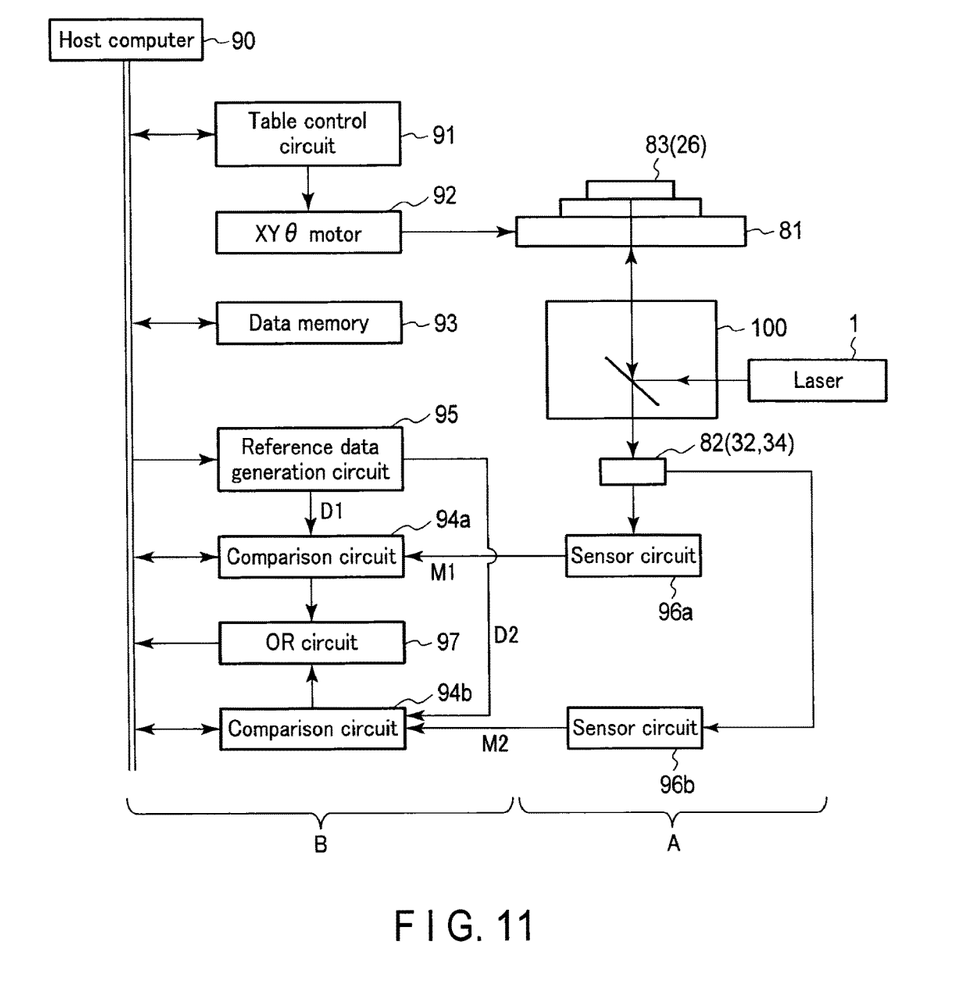
FIG. 11 is a schematic view illustrating a defect inspection device according to a sixth embodiment.

Referring to FIG. 11, the basic configuration of the defect inspection device is described. Here, a pattern inspection device for a photomask, which inspects a pattern, for example, by comparing design data and measurement data of a photomask for use in manufacture of a large-scale LSI, is described by way of example.

The defect inspection device of the present embodiment includes a structural part A which acquires an optical image of an inspection sample 26, and a structural part B which executes a process for an inspection and executes the inspection by using the optical image acquired by this structural part A.

The structural part A includes the optical system 100 according to each of the above-described embodiments, a light source 1, a camera 82 (32 and 34), an XYθ table 81 on which a photomask 83 (inspection sample 26) is placed, and sensor circuits 96a and 96b.

In the structural part B, a host computer 90, which executes overall control of the defect inspection device, is connected to a table control circuit 91, an XYθ motor 92, a data memory 93, comparison circuits 94a and 94b, a reference data generation circuit 95 and an OR circuit 97 via a bus serving as a data transmission path.

In this defect inspection device of the present embodiment, an inspection area in a pattern, which is formed on the photomask 83, is divided into inspection stripes each having a predetermined width. In addition, the photomask 83 is placed on the XYθ table 81 so that the divided inspection stripes may be successively scanned, and an inspection is executed while a one-axis stage of the XYθ table 81 is successively moved. If this stripe inspection is finished, a step movement is executed by another one-axis stage in order to observe a neighboring stripe.

The photomask 83 is placed on the XYθ table 81. The XYθ table 81 is made movable by the host computer 90 controlling the table control circuit 91 and XYθ motor 92.

Light is radiated on the pattern formed on the photomask 83 by the light source 1 such as a DUV (ultraviolet) laser. The light reflected by the photomask 83 is made incident on the camera 82 (e.g. cameras 32 and 34 in FIG. 1, etc.) via the optical system 100. In the camera 82, a part of the stripe-shaped area of the imaginarily divided pattern is enlarged, and an optical image thereof is formed. The pattern image formed on the camera 82 is photoelectrically converted by the camera 82, and is further A/D converted by the sensor circuits 96a and 96b. In addition, measurement image data M1 and M2, which are output from the sensor circuits 96a and 96b, are sent to the comparison circuits 94a and 94b, respectively.

On the other hand, the design data, which was used when the pattern of the photomask 83 was formed, is stored in the data memory 93 such as a magnetic disk or a semiconductor memory. This design data is read out from the data memory 93 to the reference data generation circuit 95 by the host computer 90. In the reference data generation circuit 95, the read-out design data is converted to two-value or multi-value design image data D1 and D2. The design image data D1 and D2 are generated in accordance with two kinds of illuminations σ, and are delivered to the comparison circuits 94a and 94b.

The comparison circuit 94a compares the measurement image data M1 and design image data D1 according to a proper algorithm. Similarly, the comparison circuit 94b compares the measurement image data M2 and design image data D2 according to a proper algorithm. If a comparison result in the comparison circuits 94a and 94b indicates that a difference between both data exceeds a predetermined threshold, a corresponding location is determined to be defective. In addition, if a defect is found in either the comparison circuit 94a or 94b by the OR circuit 97, it is determined that the photomask 83 has a defect. Information relating to this defect (for example, coordinates of a defect, or an optical image on which defect determination is based) is saved in the data memory 93 by the control of the host computer 90. In this manner, a pattern defect of the photomask 83 is detected by a Die-to-Database method.

Incidentally, in FIG. 11, the table control circuit 91, comparison circuits 94a and 94b, reference data generation circuit 95 and OR circuit 97 are composed of electrical circuits. However, the defect inspection device does not necessarily require these electrical circuits, and at least a part of them may be replaced with software by which the host computer 90 can execute the same process. In addition, the defect inspection device can be configured by the combination of electrical circuits and software. Furthermore, the above-described electrical circuits may be composed of a computer-executable program, or a program serving as software, or may be implemented by a combination of hardware and software, or a combination with firmware. When the electrical circuits are composed of a program, this program may be stored, for example, in the data memory 93.

[7] Others

In the optical system 100 of each of the above-described embodiments, the rotary phase plate 4 and front-stage microlens array 5 are disposed close to each other. However, if the realization of this is physically difficult and a slight decrease in light use efficiently is permitted, the rotary phase plate 4 and front-stage microlens array 5 may be disposed at a distance. Specifically, for example, the enlargement optical system 70 of the branch optical path 42 in FIG. 6 may be disposed between the rotary phase plate 4 and microlens array 71.

In the optical system 100 of each of the above-described embodiments, two different kinds of illuminations σ are generated. In this case, in each embodiment, the sizes of illuminations on the inspection sample 26, that is, the illumination areas (illumination fields 27 and 28), are equal. However, in each embodiment, different illumination areas (illumination fields 27 and 28) may be adopted.

In each of the above-described embodiments, the microlens array may be replaced with a prism (axicon lens) or a diffraction optical element (diffraction grating, diffraction lens, etc.). In addition, it should suffice if the polarizing beam splitter is a branching element, and it may be a non-polarizing beam splitter or a prism. Specifically, the polarizing beam splitter of each embodiment and the polarizing beam splitters 7 and 12 of the fifth embodiment can be changed to non-polarizing beam splitters.

In each of the above-described embodiments, an object of detection for acquiring an inspection image is not necessarily limited to reflective light from the inspection sample 26, and may be transmissive light of the inspection sample 26.

The use of application of the defect inspection device of each embodiment is not limited to the inspection of a pattern defect of a mask, and may be, for example, the inspection of a pattern defect of a semiconductor wafer or a liquid crystal substrate.

In each of the above-described embodiments, a description was omitted of parts which are not directly necessary for the description of the present invention, such as device configurations and control methods. However, needless to say, necessary device configurations and control methods can selectively be used on an as-needed basis.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A detect inspection device configured to inspect a defect in a pattern of an inspection sample, comprising:
    a light source;
    a first beam splitter configured to branch light from the light source into a first optical path and a second optical path;
    a first optical system disposed on the first optical path and including a first lens having a first focal distance;
    a second optical system disposed on the second optical path and including a second lens having a second focal distance which is different from the first focal distance;
    a first aperture configured to form an illumination field of the inspection sample by light which has passed through the first optical system;
    a second aperture configured to form an illumination field of the inspection sample by light which has passed through the second optical system;
    a third optical system configured to illuminate, with a first illumination, an image of the first aperture on a first area of the inspection sample, and to illuminate, with a second illumination that is different from the first illumination, an image of the second aperture on a second area different from the first area of the inspection sample;
    a first imaging element configured to acquire light of the first area;
    a second imaging element configured to acquire light of the second area;
    a first microlens array disposed between the light source and the first beam splitter;
    a second beam splitter configured to make confluent the light of the first optical path and the light of the second optical path;
    a third beam splitter configured to branch light, which is made confluent by the second beam splitter, into a third optical path and a fourth optical path, to make light of the third optical path incident on the first aperture, and to make light of the fourth optical path incident on the second aperture; and
    a second microlens array disposed between the second beam splitter and the third beam splitter.

2. The device of claim 1, further comprising an enlargement optical system disposed between the light source and the first microlens array and configured to enlarge a beam diameter of the light passing through the second lens,
    wherein the focal distance of the second lens is longer than the focal distance of the first lens.

3. The device of claim 2, further comprising:
    a fifth beam splitter configured to branch light from the light source into a fifth optical path and a sixth optical path; and
    a sixth beam splitter configured to make confluent the light of the fifth optical path and the light of the sixth optical path,
    wherein the enlargement optical system is disposed on the sixth optical path.

4. The device of claim 3, further comprising a ½ wavelength plate disposed between the light source and the fifth beam splitter.

5. The device of claim 1, wherein the second microlens array includes two microlens arrays.

6. The device of claim 1, wherein the third optical system includes a fourth beam splitter configured to reflect light from the first and second apertures, to make the light incident on the inspection sample, to pass light from the inspection sample, and to make the light incident on the first and second imaging elements.

7. The device of claim 6, wherein the third optical system includes a ¼ wavelength plate disposed between the fourth beam splitter and the inspection sample.

8. A detect inspection device configured to inspect a defect in a pattern of an inspection sample, comprising:
    a light source;
    a first beam splitter configured to branch light from the light source into a first optical path and a second optical path;
    a first optical system disposed on the first optical path and including a first lens having a first focal distance;
    a second optical system disposed on the second optical path and including a second lens having a second focal distance which is different from the first focal distance;
    a first aperture configured to form an illumination field of the inspection sample by light which has passed through the first optical system;
    a second aperture configured to form an illumination field of the inspection sample by light which has passed through the second optical system;
    a third optical system configured to illuminate, with a first illumination, an image of the first aperture on a first area of the inspection sample, and to illuminate, with a second illumination that is different from the first illumination, an image of the second aperture on a second area different from the first area of the inspection sample;
    a first imaging element configured to acquire light of the first area;
    a second imaging element configured to acquire light of the second area;
    a second beam splitter configured to make confluent the light of the first optical path and the light of the second optical path; and
    a first microlens array disposed between the second beam splitter and the first and second apertures,
    wherein the first optical system includes a second microlens array disposed between the first beam splitter and the first lens, and
    the second optical system includes a third microlens array disposed between the first beam splitter and the second lens, and an enlargement optical system disposed between the first beam splitter and the third microlens array.

9. The device of claim 8, wherein an effective area of the third microlens array is larger than an effective area of the second microlens array.

10. The device of claim 8, wherein the first and second optical systems include a rotary phase plate disposed between the first beam splitter and the second microlens array and between the enlargement optical system and the third microlens array.

11. A detect inspection device configured to inspect a defect in a pattern of an inspection sample, comprising:
 a light source;
 a first beam splitter configured to branch light from the light source into a first optical path and a second optical path;
 a first optical system disposed on the first optical path and including a first lens having a first focal distance;
 a second optical system disposed on the second optical path and including a second lens having a second focal distance which is different from the first focal distance;
 a first aperture configured to form an illumination field of the inspection sample by light which has passed through the first optical system;
 a second aperture configured to form an illumination field of the inspection sample by light which has passed through the second optical system;
 a third optical system configured to illuminate, with a first illumination, an image of the first aperture on a first area of the inspection sample, and to illuminate, with a second illumination that is different from the first illumination, an image of the second aperture on a second area different from the first area of the inspection sample;
 a first imaging element configured to acquire light of the first area;
 a second imaging element configured to acquire light of the second area;
 a first microlens array disposed between the light source and the first beam splitter; and
 a second beam splitter configured to make confluent the light of the first optical path and the light of the second optical path,
 wherein the first optical system includes a second microlens array disposed between the second beam splitter and the first lens, and
 the second optical system includes a third microlens array disposed between the second beam splitter and the second lens.

12. The device of claim 11, wherein a pitch of elemental lenses of the third microlens array is different from a pitch of elemental lenses of the second microlens array, and
 an NA of the third microlens array is equal to an NA of the second microlens array.

13. The device of claim 11, wherein each of the second and third microlens arrays includes two microlens arrays.

14. The device of claim 11, wherein the first optical system includes a third lens disposed between the second beam splitter and the second microlens array, and
 the second optical system includes a fourth lens disposed between the second beam splitter and the third microlens array.

15. The device of claim 14, wherein the first optical system includes the first aperture disposed between the second beam splitter and the third lens, and
 the second optical system includes the second aperture disposed between the second beam splitter and the fourth lens.

16. The device of claim 15, wherein the first optical system includes a fifth lens disposed between the second beam splitter and the first aperture, and
 the second optical system includes a sixth lens disposed between the second beam splitter and the second aperture.

* * * * *